(12) United States Patent
Kramer

(10) Patent No.: US 6,595,967 B2
(45) Date of Patent: *Jul. 22, 2003

(54) COLLAPSIBLE GUIDEWIRE LUMEN

(75) Inventor: Hans W. Kramer, Temecula, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/244,352

(22) Filed: Sep. 16, 2002

(65) Prior Publication Data

US 2003/0023229 A1 Jan. 30, 2003

Related U.S. Application Data

(63) Continuation of application No. 09/775,708, filed on Feb. 1, 2001, now Pat. No. 6,450,987.

(51) Int. Cl.[7] .......................... A61M 25/00; A61M 5/00; A61M 31/00
(52) U.S. Cl. ...................................... 604/264; 604/508
(58) Field of Search ............................... 600/3; 604/43, 604/264, 280, 508, 509, 510, 523; 606/194

(56) References Cited

U.S. PATENT DOCUMENTS

| | | |
|---|---|---|
| 1,011,606 A | 12/1911 | Fulton |
| 2,148,541 A | 2/1939 | Dierker |
| 2,466,042 A | 4/1949 | Reich et al. |
| 2,672,032 A | 3/1954 | Towse |
| 2,913,009 A | 11/1959 | Kuthe |
| 3,125,096 A | 3/1964 | Antiles et al. |
| 3,425,419 A | 2/1969 | Dato |
| 3,604,419 A | 9/1971 | Diskin et al. |
| 3,612,175 A | 10/1971 | Ford et al. |
| 3,768,484 A | 10/1973 | Gawura |
| 3,839,621 A | 10/1974 | Hariu |
| 4,038,519 A | 7/1977 | Foucras |
| 4,160,455 A | 7/1979 | Law |
| 4,190,033 A | 2/1980 | Foti |
| 4,298,006 A | 11/1981 | Parks |
| 4,323,071 A | 4/1982 | Simpson et al. |
| 4,464,172 A | 8/1984 | Lichtenstein |
| 4,602,642 A | 7/1986 | O'Hara et al. |
| 4,745,922 A | 5/1988 | Taylor |
| 4,747,826 A | 5/1988 | Sassano |
| 4,762,129 A | 8/1988 | Bonzel |
| 4,781,799 A | 11/1988 | Herbert, Jr. et al. |
| 4,820,349 A | 4/1989 | Saab |

(List continued on next page.)

FOREIGN PATENT DOCUMENTS

| | | |
|---|---|---|
| AU | 730835 B2 | 3/2001 |
| AU | 739996 B2 | 10/2001 |
| AU | 734506 C | 11/2001 |

(List continued on next page.)

OTHER PUBLICATIONS

Colvett et al. "Opportunitieswith combined modality therapy for selective organ preservation in muscle–invasivebladder cancer," *Journal of Surgical Oncology* 63:200–208, 1996.

Maas et al. "Intermittent antegrade/selective cerebral perfusion during circulatory arres for repair of the aortic arch," *Perfusion*; 12: 127–132, 1997.

Today's News: "Radiant Medical Announces Data from Therapeutic Cooling Trial for Heart Attack Presented at American Heart Association Meeting," *PRNewswire*, Nov. 26, 2001.

*Primary Examiner*—Edward K. Look
*Assistant Examiner*—John K. Fristoe, Jr.
(74) *Attorney, Agent, or Firm*—Gerald W. Spinks

(57) ABSTRACT

A wire guided fluid catheter assembly having a collapsible guidewire lumen. Pressurization of a fluid lumen in the catheter assembly collapses the guidewire lumen, thereby increasing the fluid flow capacity of the catheter assembly.

6 Claims, 1 Drawing Sheet

U.S. PATENT DOCUMENTS

| | | | |
|---|---|---|---|
| 4,951,677 A | 8/1990 | Crowley et al. | |
| 5,000,734 A | 3/1991 | Boussignac et al. | |
| 5,002,531 A | 3/1991 | Bonzel | |
| 5,024,668 A | 6/1991 | Peters et al. | |
| 5,046,497 A | 9/1991 | Millar | |
| 5,089,260 A | 2/1992 | Hunter et al. | |
| 5,106,368 A | 4/1992 | Uldall et al. | |
| 5,112,438 A | 5/1992 | Bowers | |
| 5,150,706 A | 9/1992 | Cox et al. | |
| 5,151,578 A | 9/1992 | Phillips | |
| 5,180,364 A | 1/1993 | Ginsburg | |
| 5,190,539 A | 3/1993 | Fletcher et al. | |
| 5,211,631 A | 5/1993 | Sheaff | |
| 5,236,908 A | 8/1993 | Gruber et al. | |
| 5,257,977 A | 11/1993 | Eshel | |
| 5,267,341 A | 11/1993 | Shearin | |
| 5,269,758 A | 12/1993 | Taheri | |
| 5,295,949 A | 3/1994 | Hathaway | |
| 5,306,261 A | 4/1994 | Alliger et al. | |
| 5,383,854 A | 1/1995 | Safar et al. | |
| 5,395,331 A | 3/1995 | O'Neill et al. | |
| 5,405,371 A | 4/1995 | Augustine et al. | |
| 5,423,807 A | 6/1995 | Milder | |
| 5,437,673 A | 8/1995 | Baust et al. | |
| 5,443,456 A | 8/1995 | Alliger et al. | |
| 5,472,418 A * | 12/1995 | Palestrant | 604/43 |
| 5,486,208 A | 1/1996 | Ginsburg | |
| 5,496,271 A | 3/1996 | Burton et al. | |
| 5,496,311 A | 3/1996 | Abele et al. | |
| 5,520,682 A | 5/1996 | Baust et al. | |
| 5,531,776 A | 7/1996 | Ward et al. | |
| 5,536,247 A | 7/1996 | Thornton | |
| 5,549,559 A | 8/1996 | Eshel | |
| 5,554,119 A | 9/1996 | Haririson et al. | |
| 5,558,644 A | 9/1996 | Boyd et al. | |
| 5,573,532 A | 11/1996 | Chang et al. | |
| 5,578,008 A | 11/1996 | Hara | |
| 5,584,804 A | 12/1996 | Klatz et al. | |
| 5,588,438 A | 12/1996 | McKown et al. | |
| 5,622,182 A | 4/1997 | Jaffe | |
| 5,624,392 A | 4/1997 | Saab | |
| 5,630,837 A | 5/1997 | Crowley | |
| 5,643,197 A | 7/1997 | Brucker et al. | |
| 5,653,692 A | 8/1997 | Masterson et al. | |
| 5,709,654 A | 1/1998 | Klatz et al. | |
| 5,733,318 A | 3/1998 | Augustine | |
| 5,733,319 A | 3/1998 | Neilson et al. | |
| 5,735,809 A | 4/1998 | Gorsuch | |
| 5,799,661 A | 9/1998 | Boyd et al. | |
| 5,800,483 A | 9/1998 | Vought | |
| 5,800,488 A | 9/1998 | Crockett | |
| 5,800,493 A | 9/1998 | Stevens et al. | |
| 5,800,516 A | 9/1998 | Fine et al. | |
| 5,807,391 A | 9/1998 | Wijkamp | |
| 5,820,593 A | 10/1998 | Safar et al. | |
| 5,824,030 A | 10/1998 | Yang et al. | |
| 5,827,222 A | 10/1998 | Klatz et al. | |
| 5,827,269 A | 10/1998 | Saadat | |
| 5,833,673 A | 11/1998 | Ockuly et al. | |
| 5,834,465 A | 11/1998 | Olney | |
| 5,837,003 A | 11/1998 | Ginsburg | |
| 5,861,021 A | 1/1999 | Thome et al. | |
| 5,868,735 A | 2/1999 | Lafontaine | |
| 5,873,835 A | 2/1999 | Hastings et al. | |
| 5,879,316 A | 3/1999 | Safar et al. | |
| 5,879,329 A | 3/1999 | Ginsburg | |
| 5,899,898 A | 5/1999 | Arless et al. | |
| 5,899,899 A | 5/1999 | Arless et al. | |
| 5,902,268 A | 5/1999 | Saab | |
| 5,906,588 A | 5/1999 | Safar et al. | |
| 5,906,594 A | 5/1999 | Scarfone et al. | |
| 5,906,636 A | 5/1999 | Casscells, III et al. | |
| 5,913,856 A | 6/1999 | Chia et al. | |
| 5,913,885 A | 6/1999 | Klatz et al. | |
| 5,957,917 A | 9/1999 | Doiron et al. | |
| 5,957,963 A | 9/1999 | Dobak, III | |
| 5,964,751 A | 10/1999 | Amplatz et al. | |
| 5,967,976 A | 10/1999 | Larsen et al. | |
| 5,968,009 A | 10/1999 | Simán | |
| 5,971,979 A | 10/1999 | Joye et al. | |
| 5,989,238 A | 11/1999 | Ginsburg | |
| 6,007,692 A | 12/1999 | Herbert et al. | |
| 6,011,995 A | 1/2000 | Guglielmi et al. | |
| 6,019,783 A | 2/2000 | Philips et al. | |
| 6,022,336 A | 2/2000 | Zadno-Azizi et al. | |
| 6,024,740 A | 2/2000 | Lesh et al. | |
| 6,033,383 A | 3/2000 | Ginsburg | |
| 6,042,559 A | 3/2000 | Dobak, III | |
| 6,051,019 A | 4/2000 | Dobak, III | |
| 6,063,101 A | 5/2000 | Jacobsen et al. | |
| 6,096,068 A | 8/2000 | Dobak, III et al. | |
| 6,106,518 A | 8/2000 | Wittenberger et al. | |
| 6,110,168 A | 8/2000 | Ginsburg | |
| 6,126,684 A | 10/2000 | Gobin et al. | |
| 6,146,411 A | 11/2000 | Noda et al. | |
| 6,146,814 A | 11/2000 | Millet | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak, III | |
| 6,165,207 A | 12/2000 | Balding et al. | |
| 6,182,666 B1 | 2/2001 | Dobak, III | |
| 6,206,004 B1 | 3/2001 | Schmidt et al. | |
| 6,224,624 B1 | 5/2001 | Lasheras et al. | |
| 6,231,594 B1 | 5/2001 | Dae | |
| 6,231,595 B1 | 5/2001 | Dobak, III | |
| 6,235,048 B1 | 5/2001 | Dobak, III | |
| 6,238,428 B1 | 5/2001 | Werneth et al. | |
| 6,245,095 B1 | 6/2001 | Dobak, III et al. | |
| 6,251,129 B1 | 6/2001 | Dobak, III et al. | |
| 6,251,130 B1 | 6/2001 | Dobak, III et al. | |
| 6,254,626 B1 | 7/2001 | Dobak, III et al. | |
| 6,261,312 B1 | 7/2001 | Dobak, III et al. | |
| 6,264,679 B1 | 7/2001 | Keller et al. | |
| 6,287,326 B1 | 9/2001 | Pecor | |
| 6,290,697 B1 | 9/2001 | Tu et al. | |
| 6,290,717 B1 | 9/2001 | Philips | |
| 6,295,990 B1 | 10/2001 | Lewis et al. | |
| 6,299,599 B1 | 10/2001 | Pham et al. | |
| 6,306,161 B1 | 10/2001 | Ginsburg | |
| 6,312,374 B1 * | 11/2001 | von Hoffmann | 600/3 |
| 6,312,452 B1 | 11/2001 | Dobak, III et al. | |
| 6,325,818 B1 | 12/2001 | Werneth | |
| 6,338,727 B1 | 1/2002 | Noda et al. | |
| 6,355,029 B1 | 3/2002 | Joye et al. | |
| 6,364,899 B1 | 4/2002 | Dobak, III | |
| 6,368,304 B1 | 4/2002 | Aliberto et al. | |
| 6,379,378 B1 | 4/2002 | Werneth et al. | |
| 6,383,210 B1 | 5/2002 | Magers et al. | |
| 6,393,320 B2 | 5/2002 | Lasersohn et al. | |
| 6,405,080 B1 | 6/2002 | Lasersohn et al. | |
| 6,409,747 B1 | 6/2002 | Gobin et al. | |
| 6,416,533 B1 | 7/2002 | Gobin et al. | |
| 6,419,643 B1 | 7/2002 | Shimada et al. | |
| 6,428,563 B1 | 8/2002 | Keller | |
| 6,432,102 B2 | 8/2002 | Joye et al. | |
| 6,432,124 B1 | 8/2002 | Worthen et al. | |
| 6,436,130 B1 | 8/2002 | Philips et al. | |
| 6,436,131 B1 | 8/2002 | Ginsburg | |
| 6,447,474 B1 | 9/2002 | Balding | |
| 6,450,987 B1 | 9/2002 | Kramer | |

| | | |
|---|---|---|
| 6,450,990 B1 | 9/2002 | Walker et al. |
| 6,451,045 B1 | 9/2002 | Walker et al. |
| 6,454,792 B1 | 9/2002 | Noda et al. |
| 6,454,793 B1 | 9/2002 | Evans et al. |
| 6,458,150 B1 | 10/2002 | Evans et al. |
| 6,460,544 B1 | 10/2002 | Worthen |
| 6,461,347 B1 * | 10/2002 | von Hoffmann ............ 604/508 |
| 6,464,716 B1 | 10/2002 | Dobak, III et al. |
| 6,468,296 B1 | 10/2002 | Dobak, III et al. |
| 6,471,717 B1 | 10/2002 | Dobak, III et al. |
| 6,475,231 B2 | 11/2002 | Dobak, III et al. |
| 6,478,811 B1 | 11/2002 | Dobak, III et al. |
| 6,478,812 B2 | 11/2002 | Dobak, III et al. |
| 6,482,226 B1 | 11/2002 | Dobak, III |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0027333 A1 | 10/2001 | Schwartz |
| 2001/0029394 A1 | 10/2001 | Dobak, III et al. |
| 2001/0031946 A1 | 10/2001 | Walker et al. |
| 2001/0032003 A1 | 10/2001 | Pecor |
| 2001/0032004 A1 | 10/2001 | Werneth |
| 2001/0039440 A1 | 11/2001 | Lasheras et al. |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak, III |
| 2002/0004675 A1 | 1/2002 | Lasheras |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin et al. |
| 2002/0016621 A1 | 2/2002 | Werneth et al. |
| 2002/0022823 A1 | 2/2002 | Luo et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032474 A1 | 3/2002 | Dobak, III et al. |
| 2002/0040717 A1 | 4/2002 | Dobak, III |
| 2002/0045892 A1 | 4/2002 | Kramer |
| 2002/0045925 A1 | 4/2002 | Keller et al. |
| 2002/0049409 A1 | 4/2002 | Noda et al. |
| 2002/0049410 A1 | 4/2002 | Noda et al. |
| 2002/0049484 A1 | 4/2002 | Werneth et al. |
| 2002/0066458 A1 | 6/2002 | Aliberto et al. |
| 2002/0068901 A1 | 6/2002 | Werneth |
| 2002/0068964 A1 | 6/2002 | Dobak, III |
| 2002/0077665 A1 | 6/2002 | Kordis et al. |
| 2002/0077680 A1 | 6/2002 | Noda |
| 2002/0082671 A1 | 6/2002 | Magers et al. |
| 2002/0091378 A1 | 7/2002 | Dobak, III et al. |
| 2002/0091429 A1 | 7/2002 | Dobak, III et al. |
| 2002/0091430 A1 | 7/2002 | Dobak, III et al. |
| 2002/0095198 A1 | 7/2002 | Whitebrook et al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103519 A1 | 8/2002 | Dobak, III et al. |
| 2002/0111584 A1 | 8/2002 | Walker et al. |
| 2002/0111616 A1 | 8/2002 | Dea et al. |
| 2002/0111657 A1 | 8/2002 | Dae et al. |
| 2002/0116041 A1 | 8/2002 | Daoud |
| 2002/0120314 A1 | 8/2002 | Evans et al. |
| 2002/0128698 A1 | 9/2002 | Dobak, III et al. |
| 2002/0138122 A1 | 9/2002 | Worthen et al. |
| 2002/0151845 A1 | 10/2002 | Werneth |
| 2002/0151945 A1 | 10/2002 | Gobin et al. |
| 2002/0151946 A1 | 10/2002 | Dobak, III |
| 2002/0156421 A1 | 10/2002 | Noda et al. |
| 2002/0156469 A1 | 10/2002 | Yon et al. |
| 2002/0161331 A1 | 10/2002 | Noda et al. |
| 2002/0169489 A1 | 11/2002 | Dobak, III et al. |
| 2002/0169490 A1 | 11/2002 | Noda et al. |
| 2002/0173834 A1 | 11/2002 | Noda et al. |

FOREIGN PATENT DOCUMENTS

| | | |
|---|---|---|
| AU | 743945 B2 | 2/2002 |
| AU | 748985 B2 | 6/2002 |
| EP | 10205167 A2 | 5/2002 |
| EP | 1029520 B1 | 8/2002 |
| WO | WO 91/05528 | 5/1991 |
| WO | WO 94/16760 | 8/1994 |
| WO | WO 96/40347 | 12/1996 |
| WO | WO 97/25011 | 7/1997 |
| WO | WO 98/26831 | 6/1998 |
| WO | WO 98/31312 | 7/1998 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 02/07793 | 1/2002 |

| | | | | | | |
|---|---|---|---|---|---|---|
| WO | WO 02/26175 | 4/2002 | | WO | WO 02/47577 | 6/2002 |
| WO | WO 02/26176 | 4/2002 | | WO | WO 02/47742 | 6/2002 |
| WO | WO 02/26285 | 4/2002 | | WO | WO 02/055129 | 7/2002 |
| WO | WO 02/26307 | 4/2002 | | WO | WO 02/056938 | 7/2002 |
| WO | WO 02/28300 | 4/2002 | | WO | WO 02/058606 | 8/2002 |
| WO | WO 02/36180 | 5/2002 | | WO | WO 02/060514 | 8/2002 |
| WO | WO 02/38091 | 5/2002 | | | | |
| WO | WO 02/43577 | 6/2002 | | | | |

* cited by examiner

COLLAPSIBLE GUIDEWIRE LUMEN

CROSS REFERENCE TO RELATED APPLICATIONS

This application is a continuation of U.S. Ser. No. 09/775,708, filed Feb. 1, 2001, now U.S. Pat. No. 6,450,987, for "Collapsible Guidewire Lumen".

STATEMENT REGARDING FEDERALLY SPONSORED RESEARCH OR DEVELOPMENT

Not Applicable

BACKGROUND OF THE INVENTION

1. Field of the Invention

This invention is in the field of wire guided fluid catheter assemblies.

2. Background Art

In conventional wire guided fluid catheter assemblies intended for insertion into a vascular system of a patient, such as into blood vessels, the tubular catheter body has at least one lumen provided for the passage of a guidewire. This guidewire lumen usually passes either through the main lumen of the catheter or along the outer surface of the main catheter body. Where the guidewire lumen passes through the main lumen of the catheter, the guidewire lumen occupies space within the catheter body that would otherwise be available for the flow of fluid, thereby reducing the fluid flow capacity of a given diameter catheter body. Put differently, a catheter assembly having a given fluid flow capacity must have a larger diameter catheter body, because of the presence of the guidewire lumen.

Similarly, where the guidewire lumen is positioned along the outer surface of the main catheter body, the presence of the guidewire lumen reduces the space available for the fluid lumen, in a catheter assembly having a given overall diameter. Said differently, the outer diameter of a catheter assembly having a given fluid flow capacity is increased by the presence of the guidewire lumen on the outer surface of the catheter body.

In either case, either the fluid flow capacity of the catheter assembly is reduced, or the minimum size blood vessel in which the catheter assembly can be used is increased, thereby limiting its usefulness.

It would be beneficial to have a catheter assembly in which the guidewire lumen does not reduce or limit the available space for the fluid lumen, and which does not add to the overall diameter of the catheter assembly. Such an assembly would maximize the fluid flow capacity of a catheter sized for insertion into any given size blood vessel.

BRIEF SUMMARY OF THE INVENTION

The present invention is a wire guided catheter assembly in which the guidewire lumen is adapted to collapse upon pressurization of the fluid lumen, thereby maximizing the size of the flow path available for fluid flow. The guidewire lumen is formed within the main catheter body, and within the fluid flow lumen. The entire catheter body can be used as a fluid flow lumen, or a separate fluid flow lumen may be established within a portion of the catheter body. In either case, the guidewire lumen is within the fluid flow lumen. In its expanded state, the guidewire lumen occupies a significant portion of the fluid flow lumen. In its collapsed state, the guidewire lumen occupies a very insignificant portion, or almost none, of the fluid flow lumen.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
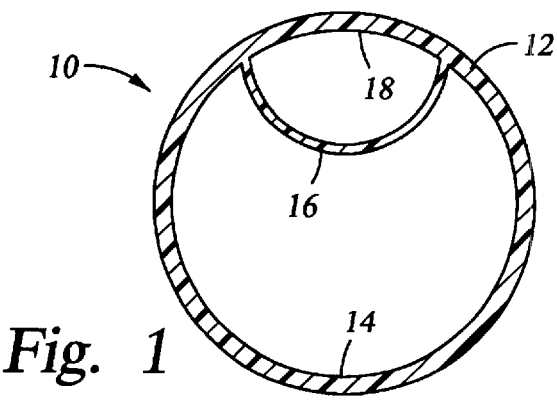
FIG. 1 is a transverse section view of a first embodiment of a catheter assembly according to the present invention, with the guidewire lumen attached to the inside of the main body of the catheter.

As seen in FIG. 1, the first embodiment of the catheter assembly 10 according to the present invention has a main catheter body 12, which encompasses a fluid flow lumen 14. Further, the main catheter body 12 encompasses a guidewire lumen 18, which is formed in part by a guidewire lumen wall 16 and in part by a portion of the main catheter body 12. The guidewire lumen wall 16 is constructed of a relatively flexible material, and with a relatively thin wall thickness, preferably for example in the range of 0.0015 inch to 0.0020 inch. The guidewire lumen wall 16 is shown fully distended, resulting in the guidewire lumen 18 being in its expanded state. In this condition, the guidewire lumen 18 is best suited for the passage of a guidewire (not shown), facilitating the insertion of the catheter assembly 10 through a vascular system of a patient. It can be seen that, when the guidewire lumen 18 is in its expanded state, the guidewire lumen 18 occupies a significant portion of the cross sectional area of the catheter body 12, thereby significantly reducing the cross sectional area which would be available for the fluid flow lumen 14. Therefore, for a given diameter of the catheter body 12, the available fluid flow capacity through the fluid flow lumen 14 is significantly limited by the expansion of the guidewire lumen 18.

Figure 2:
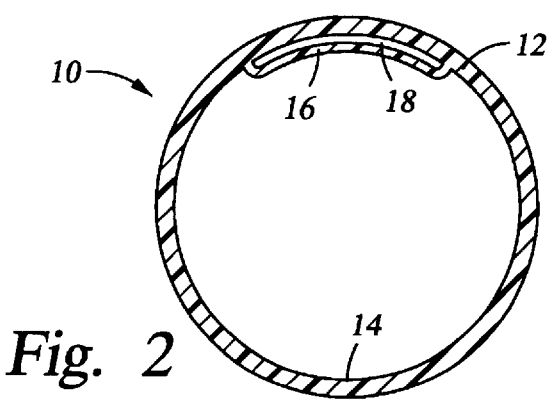
FIG. 2 is a transverse section view of the embodiment shown in FIG. 1, with the guidewire lumen in its collapsed state.

Once the catheter assembly 10 has been inserted to a desired point in the vascular system of the patient, the fluid flow lumen 14 can be pressurized with fluid, to a pressure sufficient to cause the guidewire lumen wall 16 to flex or move toward the guidewire lumen 18, thereby collapsing the guidewire lumen 18 as shown in FIG. 2. The pressure necessary for causing the collapse of the guidewire lumen 18 may be approximately 30 psig. The guidewire can be removed from the guidewire lumen 18 before pressurization of the fluid flow lumen 14, thereby allowing the guidewire lumen 18 to fully collapse. It can be seen that, with the guidewire lumen 18 collapsed, the cross sectional area of the catheter body 12 available for the fluid flow lumen 14 has significantly increased, essentially maximizing the fluid flow capacity of the catheter assembly 10 for a given overall diameter. When it is desired to again insert the guidewire into the guidewire lumen 18, the guidewire lumen 18 can be returned to its expanded state, shown in FIG. 1, by pressurizing the guidewire lumen 18 with a fluid such as a saline solution.

Figure 3:
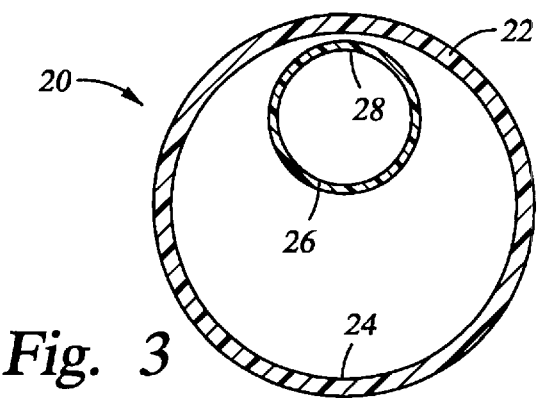
FIG. 3 is a transverse section view of a second embodiment of a catheter assembly according to the present invention, with the guidewire lumen separately formed within the main body of the catheter.

As seen in FIG. 3, a second embodiment of the catheter assembly 20 according to the present invention has a main catheter body 22, which encompasses a fluid flow lumen 24. Further, the main catheter body 22 encompasses a guidewire lumen 28, which is formed entirely by a tubular guidewire passageway 26 separately formed within the fluid flow lumen 24 of the main catheter body 22. The tubular guidewire passageway 26 is constructed of a relatively flexible material, and with a relatively thin wall thickness, preferably for example in the range of 0.0015 inch to 0.0020 inch. The tubular guidewire passageway 26 is shown fully distended, resulting in the guidewire lumen 28 being in its expanded state. In this condition, the guidewire lumen 28 is best suited for the passage of a guidewire (not shown), facilitating the insertion of the catheter assembly 20 through a vascular system of a patient. It can be seen that, when the guidewire lumen 28 is in its expanded state, the guidewire lumen 28 occupies a significant portion of the cross sectional area of the catheter body 22, thereby significantly reducing the cross sectional area which would be available for the fluid flow lumen 24. Therefore, for a given diameter of the catheter body 22, the available fluid flow capacity through the fluid flow lumen 24 is significantly limited by the expansion of the guidewire lumen 28.

Figure 4:
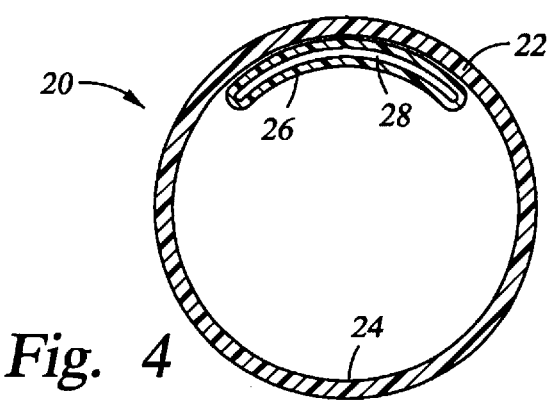
FIG. 4 is a transverse section view of the embodiment shown in FIG. 3, with the guidewire lumen in its collapsed state.

Once the catheter assembly 20 has been inserted to a desired point in the vascular system of the patient, the fluid flow lumen 24 can be pressurized with fluid, to a pressure sufficient to cause the tubular guidewire passageway 26 to flex or move into the guidewire lumen 28, thereby collapsing the guidewire lumen 28 as shown in FIG. 4. The pressure necessary for causing the collapse of the guidewire lumen 28 may be approximately 30 psig. The guidewire can be removed from the guidewire lumen 28 before pressurization of the fluid flow lumen 24, thereby allowing the guidewire lumen 28 to fully collapse. It can be seen that, with the guidewire lumen 28 collapsed, the cross sectional area of the catheter body 22 available for the fluid flow lumen 24 has significantly increased, essentially maximizing the fluid flow capacity of the catheter assembly 20 for a given overall diameter. When it is desired to again insert the guidewire into the guidewire lumen 28, the guidewire lumen 28 can be returned to its expanded state, shown in FIG. 3, by pressurizing the guidewire lumen 28 with a fluid.

Figure 5:
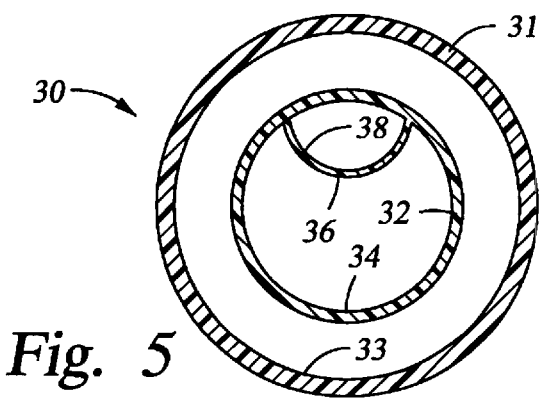
FIG. 5 is a transverse section view of a third embodiment of a catheter assembly according to the present invention, with the fluid lumen separately formed within the main body of the catheter, and the guidewire lumen attached to the inside of the fluid lumen.

As seen in FIG. 5, a third embodiment of the catheter assembly 30 according to the present invention has a main catheter body 31, which encompasses a main catheter lumen 33. The main catheter lumen 33 can be utilized for the return of fluid through the catheter assembly 30, or for any other purpose. The main catheter body 31 also encompasses a fluid flow lumen 34, which is formed by a separate tubular fluid flow passageway 32 within the main catheter lumen 33. Further, the main catheter body 31 and the tubular fluid flow passageway 32 both encompass a guidewire lumen 38, which is formed in part by a guidewire lumen wall 36 and in part by a portion of the tubular fluid flow passageway 32. The guidewire lumen wall 36 is constructed of a relatively flexible material, and with a relatively thin wall thickness, preferably for example in the range of 0.0015 inch to 0.0020 inch. The guidewire lumen wall 36 is shown fully distended, resulting in the guidewire lumen 38 being in its expanded state. In this condition, the guidewire lumen 38 is best suited for the passage of a guidewire (not shown), facilitating the insertion of the catheter assembly 30 through a vascular system of a patient. It can be seen that, when the guidewire lumen 38 is in its expanded state, the guidewire lumen 38 occupies a significant portion of the cross sectional area of the tubular fluid flow passageway 32, thereby significantly reducing the cross sectional area which would be available for the fluid flow lumen 34. Therefore, for a given diameter of the catheter body 31, and for a given diameter of the tubular fluid flow passageway 32, the available fluid flow capacity through the fluid flow lumen 34 is significantly limited by the expansion of the guidewire lumen 38.

Figure 6:
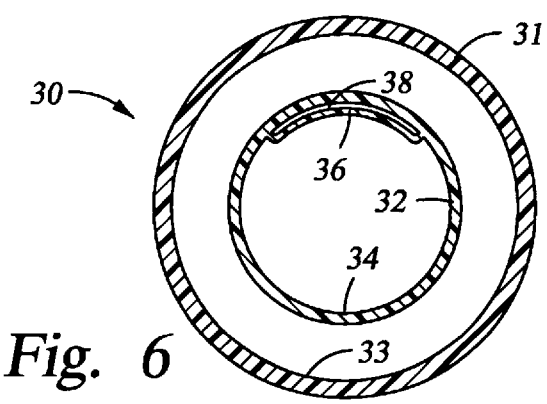
FIG. 6 is a transverse section view of the embodiment shown in FIG. 5, with the guidewire lumen in its collapsed state.

Once the catheter assembly 30 has been inserted to a desired point in the vascular system of the patient, the fluid flow lumen 34 can be pressurized with fluid, to a pressure sufficient to cause the guidewire lumen wall 36 to flex or move toward the guidewire lumen 38, thereby collapsing the guidewire lumen 38 as shown in FIG. 6. The pressure necessary for causing the collapse of the guidewire lumen 38 may be approximately 30 psig. The guidewire can be removed from the guidewire lumen 38 before pressurization of the fluid flow lumen 34, thereby allowing the guidewire lumen 38 to fully collapse. It can be seen that, with the guidewire lumen 38 collapsed, the cross sectional area of the tubular fluid flow passageway 32 available for the fluid flow lumen 34 has significantly increased, essentially maximizing the fluid flow capacity of the catheter assembly 30 for a given overall diameter. When it is desired to again insert the guidewire into the guidewire lumen 38, the guidewire lumen 38 can be returned to its expanded state, shown in FIG. 5, by pressurizing the guidewire lumen 38 with a fluid such as a saline solution.

Figure 7:
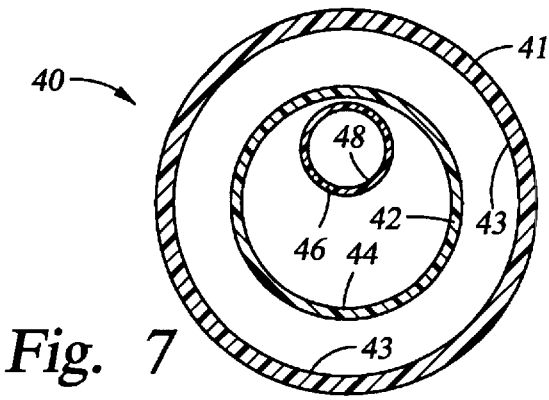
FIG. 7 is a transverse section view of a fourth embodiment of a catheter assembly according to the present invention, with the fluid lumen separately formed within the main body of the catheter, and the guidewire lumen separately formed within the fluid lumen.

As seen in FIG. 7, a fourth embodiment of the catheter assembly 40 according to the present invention has a main catheter body 41, which encompasses a main catheter lumen 43. The main catheter lumen 43 can be utilized for the return of fluid through the catheter assembly 40, or for any other purpose. The main catheter body 41 also encompasses a fluid flow lumen 44, which is formed by a separate tubular fluid flow passageway 42 within the main catheter lumen 43. Further, the main catheter body 41 and the tubular fluid flow passageway 42 both encompass a guidewire lumen 48, which is formed entirely by a tubular guidewire passageway 46 separately formed within the fluid flow lumen 44 of the tubular fluid flow passageway 42. The tubular guidewire passageway 46 is constructed of a relatively flexible material, and with a relatively thin wall thickness, preferably for example in the range of 0.0015 inch to 0.0020 inch. The tubular guidewire passageway 46 is shown fully distended, resulting in the guidewire lumen 48 being in its expanded state. In this condition, the guidewire lumen 48 is best suited for the passage of a guidewire (not shown), facilitating the insertion of the catheter assembly 40 through a vascular system of a patient. It can be seen that, when the guidewire lumen 48 is in its expanded state, the, guidewire lumen 48 occupies a significant portion of the cross sectional area of the tubular fluid flow passageway 42, thereby significantly reducing the cross sectional area which would be available for the fluid flow lumen 44. Therefore, for a given diameter of the catheter body 41, and for a given diameter of the tubular fluid flow passageway 42, the available fluid flow capacity through the fluid flow lumen 44 is significantly limited by the expansion of the guidewire lumen 48.

Figure 8:
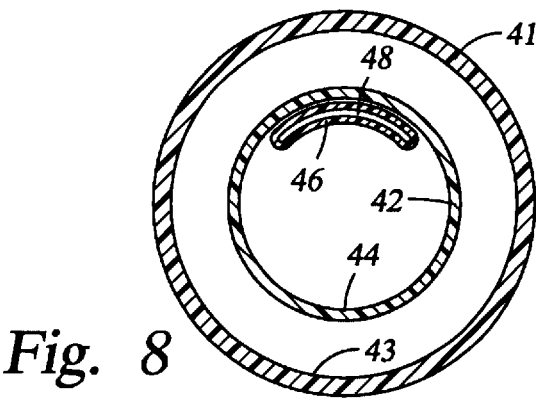
FIG. 8 is a transverse section view of the embodiment shown in FIG. 7, with the guidewire lumen in its collapsed state.

Once the catheter assembly 40 has been inserted to a desired point in the vascular system of the patient, the fluid flow lumen 44 can be pressurized with fluid, to a pressure sufficient to cause the tubular guidewire passageway 46 to flex or move into the guidewire lumen 48, thereby collapsing the guidewire lumen 48 as shown in FIG. 8. The pressure necessary for causing the collapse of the guidewire lumen 48 may be approximately 30 psig. The guidewire can be removed from the guidewire lumen 48 before pressurization of the fluid flow lumen 44, thereby allowing the guidewire lumen 48 to fully collapse. It can be seen that, with the guidewire lumen 48 collapsed, the cross sectional area of the tubular fluid flow passageway 42 available for the fluid flow lumen 44 has significantly increased, essentially maximizing the fluid flow capacity of the catheter assembly 40 for a given overall diameter. When it is desired to again insert the guidewire into the guidewire lumen 48, the guidewire lumen 48 can be returned to its expanded state, shown in FIG. 7, by pressurizing the guidewire lumen 48 with a fluid.

While the invention as herein shown and disclosed is fully capable of providing the advantages hereinbefore stated, it is to be understood that this disclosure is merely illustrative of the presently preferred embodiments of the invention and that no limitations are intended other than as described in the appended claims.

I claim:

1. A catheter assembly comprising: a catheter body; a first longitudinal lumen encompassed within said catheter body; a second longitudinal lumen formed within said catheter body, said second lumen being separated from said first lumen by a wall of said second lumen; wherein said second lumen wall is adapted to move toward said second lumen, upon creation of a higher pressure in said first lumen than in said second lumen; and, wherein said first lumen is at least partially defined by an inner conduit within said catheter body.

2. The catheter assembly recited in claim 1, wherein said second lumen wall is formed as a longitudinal partition across said inner conduit, thereby partitioning said second lumen from said first lumen.

3. The catheter assembly recited in claim 1, wherein said second lumen wall is formed as a flexible tube within said inner conduit, thereby defining said second lumen substantially surrounded by said first lumen.

4. A method for treating an organ of a patient, said method comprising:

providing a catheter having a body having first and second longitudinal lumens therein;

introducing said catheter into an organ of a patient;

creating a higher pressure in said first lumen than in said second lumen, thereby moving a wall of said second lumen into said second lumen, to collapse said second lumen, said first lumen is at least partially defined by an inner conduit within the body of said catheter.

5. The method recited in claim 4, wherein:

said second lumen wall is formed as a longitudinal partition across said inner conduit, thereby partitioning said second lumen from said first lumen;

said method further comprising flexing said second lumen wall to substantially conform to said inner conduit, with said creation of said higher pressure in said first lumen, thereby expanding said first lumen to occupy substantially the entirety of said inner conduit.

6. The method recited in claim 4, wherein:

said second lumen wall is formed as a flexible tube within said inner conduit, thereby defining said second lumen substantially surrounded by said first lumen;

said method further comprising collapsing said flexible tube, with said creation of said higher pressure in said first lumen, thereby expanding said first lumen to occupy substantially the entirety of said inner conduit.

* * * * *